US012781266B2

(12) United States Patent
Thompson et al.

(10) Patent No.: US 12,781,266 B2
(45) Date of Patent: Nov. 3, 2026

(54) SYNTHETIC POLYNUCLEOTIDES AND METHOD OF USE THEREOF IN GENETIC ANALYSIS

(71) Applicant: PERSONAL GENOME DIAGNOSTICS INC., Baltimore, MD (US)

(72) Inventors: John Thompson, Baltimore, MD (US); Derek Murphy, Baltimore, MD (US); Gustavo Cerqueira, Baltimore, MD (US); Cindy Maddox, Baltimore, MD (US); Laurel Keefer, Baltimore, MD (US)

(73) Assignee: PERSONAL GENOME DIAGNOSTICS INC., Baltimore, MD (US)

( * ) Notice: Subject to any disclaimer, the term of this patent is extended or adjusted under 35 U.S.C. 154(b) by 766 days.

(21) Appl. No.: 17/669,988

(22) Filed: Feb. 11, 2022

(65) Prior Publication Data

US 2022/0356513 A1 Nov. 10, 2022

Related U.S. Application Data

(60) Provisional application No. 63/185,732, filed on May 7, 2021.

(51) Int. Cl.

| | |
|---|---|
| ***C12Q 1/6827*** | (2018.01) |
| ***C12Q 1/6883*** | (2018.01) |
| ***C12Q 1/6886*** | (2018.01) |

(52) U.S. Cl.

CPC ......... *C12Q 1/6827* (2013.01); *C12Q 1/6886* (2013.01); *C12Q 1/6883* (2013.01);

(Continued)

(58) Field of Classification Search

None

See application file for complete search history.

(56) References Cited

FOREIGN PATENT DOCUMENTS

| | | | |
|---|---|---|---|
| JP | 2007528227 | A | 10/2007 |
| JP | 2017537646 | A | 12/2017 |

(Continued)

OTHER PUBLICATIONS

Coudray-Meunier et al, "A comparative study of digital RT-PCR and RT-qPCR for quantification of Hepatitis A virus and Norovirus in lettuce and water samples", International Journal of Food Microbiology 2015 (Year: 2015).*

(Continued)

*Primary Examiner* — Heather Calamita

*Assistant Examiner* — Elizabeth Rose Lafave

(74) *Attorney, Agent, or Firm* — Kilpatrick Townsend & Stockton LLP

(57) ABSTRACT

The disclosure provides a synthetic standard which includes polynucleotides (e.g., DNA or RNA) containing multiple clinically important germline and somatic variants. These materials are utilized to calibrate, evaluate, and/or validate the performance of polynucleotide-based genetic analysis assays, such as NGS assays. In one aspect the disclosure provides a method for validating assay performance including generating synthetic variant DNA fragments comprising variants with known allele frequencies, wherein the fragments comprise a molecular tag; combining the synthetic variant DNA with wild-type DNA to create test samples; preparing one or more dilutions of the test samples; performing an assay of interest on the one or more dilutions of test samples; and comparing the outcome of the assay with the test samples with known allele frequencies of interest, thereby validating the performance of the assay.

23 Claims, 6 Drawing Sheets

(52) U.S. Cl.
CPC . *C12Q 2545/101* (2013.01); *C12Q 2600/106* (2013.01); *C12Q 2600/156* (2013.01); *C12Q 2600/166* (2013.01)

(56) References Cited

FOREIGN PATENT DOCUMENTS

| | | | | | |
|---|---|---|---|---|---|
| JP | 2019534051 | A | | 11/2019 | |
| KR | 20200128194 | A | | 11/2020 | |
| WO | WO-9511995 | A1 | * | 5/1995 | ............. B82Y 30/00 |
| WO | WO-2017205827 | A1 | * | 11/2017 | .......... B01J 19/0046 |
| WO | 2017223366 | A1 | | 12/2017 | |

OTHER PUBLICATIONS

Ossandon et al, "Circulating Tumor DNA Assays in Clinical Cancer Research", Journal of the National Cancer Institute 2018 (Year: 2018).*
Tong et al, "Drug combination approach to overcome resistance to EGFR tyrosine kinase inhibitors in lung cancer", Cancer Letters 2017 (Year: 2017).*
Deveson, et al., "Evaluating the Analytical Validity of Circulating Tumor DNA Sequencing Assays for Precision Oncology", Nature Biotechnology, vol. 39, Apr. 12, 2021, pp. 1115-1128.
First Examination Report issued in GB 2318728.9 date Nov. 7, 2024, 2 pages.
Masser, et al., "Focused, High Accuracy 5-Methylcytosine Quantitation with Base Resolution by Benchtop Next-Generation Sequencing", Epigenetics & Chromatin, vol. 6, No. 1, Oct. 11, 2013, 12 pages.
International Preliminary Report on Patentability issued in PCT/US2022/016177 dated Nov. 16, 2023, 9 pages.
International Search Report and Written Opinion issued in PCT/US2022/16177 dated May 18, 2022, 11 pages.
Balckburn et al., "Use of Synthetic DNA Spike-in Controls (Sequins) for Human Genome Sequencing", Nature Protocols, Nature Publishing Group, GB, vol. 14, No. 7, Jul. 2019, pp. 2119-2151.
Chen et al., "The Overlooked Fact: Fundamental Need for Spike-In Control for Virtually All Genome-Wide Analyses", Molecular and Cellular Biology, vol. 36, No. 5, Mar. 2016, pp. 662-667.
EP22799247.6, "Extended European Search Report", Jul. 28, 2025, 12 pages.
Jiang et al., "Synthetic Spike-in Standards for RNA-Seq Experiments", Genome Research, vol. 21, No. 9, Aug. 4, 2011, pp. 1543-1551.
Verma et al., "Analytical Performance Evaluation of a Commercial Next Generation Sequencing Liquid Biopsy Platform Using Plasma CTDNA, Reference Standards, and Synthetic Serial Dilution Samples Derived From Normal Plasma", BioMed Central Cancer, vol. 20, Article 945, Available Online at: https://link.springer.com/article/10.1186/s12885-020-07445-5/fulltext.html, Oct. 1, 2020, pp. 1-15.
Office Action issued in GB2318728.9 dated Apr. 14, 2025, 4 pages.
Parpart-Li, et al., "A Method for Comprehensive Genomic Analysis of Cell-Free DNA", Journal of Clinical Oncology, vol. 33, No. 15, E22070, Online Available at: 10.1200/jco.2015.33.15_suppl.e22070, May 20, 2015.
JP2023-568285, "Office Action", Nov. 21, 2025, 14 pages.
KR Patent Application No. 10-2023-7041847, "Office Action", mailed Jul. 3, 2026, 22 pages, with English translation.

* cited by examiner

- Synthetic sample can be restricted to coding exons of genes affected by CNV
- CNV methods does not require distinct coverage. We still recommend applying sliding windows approach, in case distinct coverage is eventually taken into account by CNV detections methods.
- Different proportions of normal and mutant dictates the CNV fold change.

SYNTHETIC POLYNUCLEOTIDES AND METHOD OF USE THEREOF IN GENETIC ANALYSIS

CROSS-REFERENCE TO RELATED APPLICATION(S)

This application claims the benefit of priority under 35 U.S.C. § 119 (e) of U.S. Provisional Patent Application Ser. No. 63/185,732, filed May 7, 2021. The disclosure of the prior application is considered part of and is incorporated by reference in the disclosure of this application.

BACKGROUND OF THE INVENTION

Field of the Invention

The invention relates generally to genetic analysis and more specifically to a method of use of synthetic polynucleotides to develop and evaluate performance metrics of genetic analysis assays.

Background Information

Contrived clinical and cell-line samples are utilized during next-generation sequencing (NGS) assay development to train and evaluate the performance of the assay when clinical samples containing target variants of interest are difficult or impossible to obtain. These contrived samples are also created to address the biological limitations of clinical patient plasma, namely, the low yields of circulating cell-free DNA (cfDNA) and the limited number of actionable alterations detectable in a single clinical specimen.

Current methods for the creation of contrived cfDNA samples are imprecise, expensive, and labor intensive. The contrived sample creation process involves the pre-characterization of cell lines and/or clinical samples with NGS-based assays to identify the comprehensive mutational signature of each sample. Once the signature for each sample has been obtained, cell lines or clinical samples containing the specific variants of interest are combined in specific ratios to achieve the desired representation of the variants in a final contrived blend. Once these blended samples are created, they are again pre-characterized to ensure they contain the variants of interest at the specified levels of interest before enrollment in analytical assay development studies.

Each created contrived blend will typically contain a small number of variants and each variant type (SNVs/INDELs, Translocations and Amplification) needs to be represented by distinct contrived blends. Therefore, a multitude of contrived sample blends are often needed to train and validate the performance of comprehensive NGS assays. An additional limitation of using cell line blends in NGS assays is that, while renewable, they do not provide the proper size distribution to mimic cfDNA.

Development of cfDNA assay technologies, such as high-throughput NGS, qPCR or digital PCR, enables the profiling of cfDNA samples. However, performance evaluation and comparison between different assays can be challenging due to sample variability and technology bias. Genetic analysis assays that are more robust and clinically relevant due to the ability to calibrate, evaluate, and validate assay performance are needed.

SUMMARY OF THE INVENTION

The present disclosure provides a method of using synthetic polynucleotides to address the limitations of use of contrived clinical and cell-line samples during genetic analysis assay development to train and evaluate the performance of the assay when clinical samples containing target variants of interest are difficult or impossible to obtain. The present disclosure describes the generation of synthetic polynucleotide (e.g., DNA) samples containing multiple clinically important germline and somatic variants. These materials are utilized to calibrate, evaluate, and/or validate the performance of polynucleotide-based genetic analysis assays, such as NGS assays.

In an embodiment, the present disclosure provides a method for validating assay performance using synthetic polynucleotides, such as DNA fragments. The method includes: generating synthetic variant DNA fragments including variants with known allele frequencies, wherein the fragments include a molecular tag; combining the synthetic variant DNA with wild-type DNA to create test samples; preparing one or more dilutions of the test samples; performing an assay of interest on the one or more dilutions of test samples; and comparing the outcome of the assay with the test samples with known allele frequencies of interest, thereby validating the performance of the assay.

In another embodiment, the present disclosure provides a method of detecting a disease or disorder, or severity of a disease or disorder, in a subject. The method includes: validating assay performance using the method of the disclosure, wherein the assay of interest detects a disease or disorder, or severity of a disease or disorder; obtaining a sample from the subject; and performing the validated assay on DNA of the sample from the subject and detecting a target of interest indicative of a disease or disorder, or severity of a disease or disorder, thereby detecting a disease or disorder, or severity of a disease or disorder in the subject.

In yet another embodiment, the present disclosure provides a method of detecting drug resistance in a subject. The method includes: validating assay performance using the method of the disclosure, wherein the assay of interest detects drug resistance; obtaining a sample from the subject; and performing the validated assay on DNA of the sample from the subject and detecting a target of interest indicative of drug resistance, thereby detecting drug resistance in the subject.

DETAILED DESCRIPTION OF THE INVENTION

Figure 1:
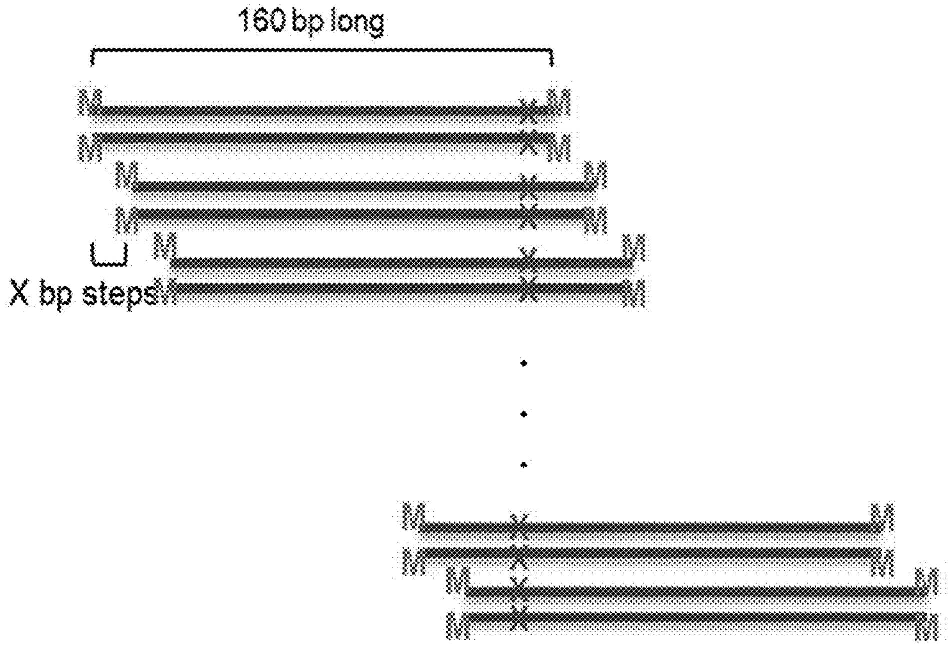
FIG. 1 is a schematic showing the presence of a molecular tag at the 3' and 5' ends of synthetic DNA molecules which allows for the identification of the molecules as synthetic post-sequencing.

The present disclosure describes generation of a synthetic standard which includes polynucleotides (e.g., DNA or RNA) containing multiple clinically important germline and somatic variants. These materials are utilized to calibrate, evaluate, and/or validate the performance of polynucleotide-based genetic analysis assays, such as NGS assays.

Before the present compositions and methods are described, it is to be understood that this invention is not limited to the particular compositions, methods and experimental conditions described, as such compositions, methods, and conditions may vary. It is also to be understood that the terminology used herein is for purposes of describing particular aspects and embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth. For the purpose of further illustration, the term "a target nucleic acid" includes a plurality of target nucleic acids, including mixtures thereof.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present disclosure provides an innovative method using synthetic polynucleotides, such as DNA, in a standard in the development and implementation of genetic analysis assays to train and evaluate the performance of the assay.

The terms "standard," "reference," or "synthetic sample," as used herein, generally refer to a substance which is prepared to certain pre-defined criteria and can be used to assess certain aspects of, for example, an assay. Standards or references preferably yield reproducible, consistent and reliable results. These aspects may include performance metrics, examples of which include, but are not limited to, accuracy, specificity, sensitivity, linearity, reproducibility, and limit of detection or limit of quantitation. Standards or references may be used for assay development, assay validation, and/or assay optimization. Standards may be used to evaluate quantitative and qualitative aspects of an assay. It will be appreciated that standards may be used in any application in which a defined reference is necessary and/or useful. In some aspects, applications may include monitoring, comparing and/or otherwise assessing a QC sample/control, an assay control (product), a filler sample, a training sample, and/or lot-to-lot performance for a given assay.

The terms "polynucleotide", "nucleic acid" and "oligonucleotide" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, cell-free polynucleotides including cfDNA and cell-free RNA (cfRNA), nucleic acid probes, and primers. A polynucleotide may include one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In one embodiment, the present disclosure describes the design and use of a synthetic cfDNA sample, also referred to herein as a standard or reference, which contains multiple alterations of interest in a single sample set. Design and development of these materials mitigates the need to source, pre-characterize, blend and dilute the multitude of clinical or cell line samples necessary to obtain the desired variants of interest. The synthetic standard streamlines the manufacturing of contrived materials and dramatically reduces costs associated with the process. In addition, by evaluating multiple variants and variant types in a single specimen, a reduced number of assay reactions and sequencing runs are needed to analytically validate an assay. This can result in reduced costs and shorter development times for assay development.

The term "cell-free nucleic acid" or "CFNA" refers to extracellular nucleic acids, as well as circulating free nucleic acid. As such, the terms "extracellular nucleic acid," "cell-free nucleic acid" and "circulating free nucleic acid" are used interchangeably. Extracellular nucleic acids can be found in biological sources such as blood, urine, and stool. CFNA may refer to cell-free DNA (cfDNA), circulating free DNA (cfDNA), cell-free RNA (cfRNA), or circulating free RNA (cfRNA). CFNA may result from the shedding of nucleic acids from cells undergoing apoptosis or necrosis. Previous studies have demonstrated that CFNA, for example cfDNA, exists at steady-state levels and can increase with cellular injury or necrosis. In some cases, CFNA is shed from abnormal cells or unhealthy cells, such as tumor cells, cfDNA shed from tumor cells, in some cases, can be distinguished from cfDNA shed from normal or healthy cells using genomic information, such as by identifying genetic variations including mutations and/or gene fusions distinguishing between normal and abnormal cells, as well as additional discriminators such as polynucleotide length, end position, and base modifications (e.g., methylation, hydroxymethylation, formylation, carboxylation, and the like). In some cases, CFNA is shed from cells associated with a fetus into maternal circulation. In some cases, CFNA may originate from a pathogen that has infected a host, such as a subject (e.g., patient).

The term "mutant" or "variant," when made in reference to an allele or sequence, generally refers to an allele or sequence that does not encode the phenotype most common in a particular natural population. The terms "mutant allele" and "variant allele" can be used interchangeably. In some cases, a mutant allele can refer to an allele present at a lower frequency in a population relative to the wild-type allele. In some cases, a mutant allele or sequence can refer to an allele or sequence mutated from a wild-type sequence to a mutated sequence that presents a phenotype associated with a disease state and/or drug resistant state. Mutant alleles and sequences may be different from wild-type alleles and sequences by only one base but can be different up to several bases or more. The term mutant when made in reference to a gene generally refers to one or more sequence mutations in a gene, including a point mutation, a single nucleotide polymorphism (SNP), an insertion, a deletion, a substitution, a transposition, a translocation, a copy number variation, or another genetic mutation, alteration or sequence variation.

In general, the term "sequence variant" refers to any variation in sequence relative to one or more reference sequences. Typically, the sequence variant occurs with a lower frequency than the reference sequence for a given population of individuals for whom the reference sequence is known. In some cases, the reference sequence is a single known reference sequence, such as the genomic sequence of a single individual. In some cases, the reference sequence is a consensus sequence formed by aligning multiple known sequences, such as the genomic sequence of multiple individuals serving as a reference population, or multiple sequencing reads of polynucleotides from the same individual. In some cases, the sequence variant occurs with a low frequency in the population (also referred to as a "rare" sequence variant). For example, the sequence variant may occur with a frequency of about or less than about 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower. In some cases, the sequence variant occurs with a frequency of about or less than about 0.1%. A sequence variant can be any variation with respect to a reference sequence. A sequence variation may consist of a change in, insertion of, or deletion of a single nucleotide, or of a plurality of nucleotides (e.g. 2, 3, 4, 5, 6, 7, 8, 9, 10, or more nucleotides). Where a sequence variant includes two or more nucleotide differences, the nucleotides that are different may be contiguous with one another, or discontinuous. Non-limiting examples of types of sequence variants include single nucleotide polymorphisms (SNP), deletion/insertion polymorphisms (INDEL), copy number variants (CNV), loss of heterozygosity (LOH), microsatellite instability (MSI), variable number of tandem repeats (VNTR), and retrotransposon-based insertion polymorphisms. Additional examples of types of sequence variants include those that occur within short tandem repeats (STR) and simple sequence repeats (SSR), or those occurring due to amplified fragment length polymorphisms (AFLP) or differences in epigenetic marks that can be detected (e.g. methylation differences). In some aspects, a sequence variant can refer to a chromosome rearrangement, including but not limited to a translocation or fusion gene, or fusion of multiple genes resulting from, for example, chromothripsis.

The term "allele," as used herein, refers to any of one or more alternative forms of a gene at a particular locus, all of which may relate to one trait or characteristic at the specific locus. In a diploid cell of an organism, alleles of a given gene can be located at a specific location, or locus (loci plural) on a chromosome. The sequences at these variant sites that differ between different alleles are termed "variants", "polymorphisms", or "mutations".

The terms "allele frequency" or "allelic frequency," as used herein, generally refer to the relative frequency of an allele (e.g., variant of a gene) in a sample, e.g., expressed as a fraction or percentage. In some cases, allelic frequency may refer to the relative frequency of an allele (e.g., variant of a gene) in a sample, such as a cell-free nucleic acid sample. In some cases, allelic frequency may refer to the relative frequency of an allele (e.g., variant of a gene) in a sample, such as a cell-free nucleic acid standard. The allelic frequency of a mutant allele may refer to the frequency of the mutant allele relative to the wild-type allele in a sample, e.g., a cell-free nucleic acid sample. For example, if a sample includes 100 copies of a gene, five of which are a mutant allele and 95 of which are the wild-type allele, an allelic frequency of the mutant allele is about 5/100 or about 5%. A sample having no copies of a mutant allele (e.g., about 0% allelic frequency) may be used, for example, as a negative control. A negative control may be a sample in which no mutant allele is expected to be detected. A sample including a mutant allele at about 50% allelic frequency may, for example, be representative of a germline heterozygous mutation.

The term "wild-type" when made in reference to an allele or sequence, generally refers to the allele or sequence that encodes the phenotype most common in a particular natural population. In some cases, a wild-type allele can refer to an allele present at highest frequency in the population. In some cases, a wild-type allele or sequence refers to an allele or sequence associated with a normal state relative to an abnormal state, for example a disease state.

In various aspects, the disclosure provides methods of using a CFNA standard, as well as compositions and kits including CFNA standards.

In one embodiment, the disclosure provides a method for validating assay performance using a CFNA standard that includes synthetic polynucleotides, such as synthetic DNA fragments which include genomic variants. The method includes: generating synthetic variant DNA fragments including variants with known allele frequencies, wherein the fragments include a molecular tag; combining the synthetic variant DNA with wild-type DNA to create test samples; preparing one or more dilutions of the test samples; performing an assay of interest on the one or more dilutions of test samples; and comparing the outcome of the assay with the test samples with known allele frequencies of interest, thereby validating the performance of the assay.

In various aspects, a test sample for use with the method of the invention includes CFNA (e.g., cfDNA and/or cfRNA) that is obtained from a subject, for example from a biological sample of a subject. Non-limiting examples of subjects are mammals, such as humans, non-human primates, rodents such as mice and rats, dogs, cats, pigs, sheep, rabbits and others. In some aspects, a subject is suspected of having a disease or disorder, and cell-free polynucleotides obtained from the subject may include a sequence variant associated with the disease or disorder. In some aspects, a subject is pregnant, and cell-free polynucleotides obtained from the subject include fetal polynucleotides.

While the present disclosure illustrates development and use of synthetic polynucleotide fragments in the context of CFNA analysis, it will be appreciated that synthetic polynucleotide fragments may be developed and used for analysis of many types of genetic material in addition to CFNA. In some aspects, synthetic polynucleotide fragments may be developed and utilized in assays for analysis of virtually any type of genetic material that may be obtained from a biological sample. For example, nucleic acids may be isolated from tissue, a cell or portion thereof, whole blood, plasma or serum. By way of example, a biological sample (e.g., test sample) may include, but is not limited to tissue, whole blood, serum, plasma, urine, feces, bile, breast milk, breast fluid, gastric acid, mucus, pus, rheum, saliva, semen, sputum, sweat, tears, vaginal secretion, vomit, umbilical cord blood, and endocervical fluid. In some aspects, the biological sample is a cell line, a histological slide, a biopsy sample, a formalin-fixed paraffin-embedded (FFPE) tissue, a body fluid, feces, urine, plasma, serum, whole blood, isolated blood cells, or cells isolated from blood.

It will be understood that a target nucleic acid of the sample may refer to any nucleic acid that is desired to be detected. For example, in a sample obtained from a subject having, or suspected of having a disease, such as a cancer or tumor, the target nucleic acid may refer to a variant allele known to be associated, either weakly or strongly, with the suspected cancer or tumor. In addition, in a sample obtained from a subject having, or suspected of having a drug resistant state, the target nucleic acid may refer to a sequence variant or variant allele known to be associated, either weakly or strongly, with resistance to a particular therapeutic drug or class of drugs.

In various aspects, the test sample includes cfDNA. In some aspects, the cfDNA may be purified or concentrated prior to use in a CFNA assay. For example, cfDNA may be purified or concentrated using binding resins or beads, whereby cfDNA of a desired size is retained and released in a separate volume. In various aspects, cfDNA may be selected for size (e.g., length) prior to use, for example to enrich the proportion of cfDNA fragments that are mononucleosomalin length.

Cell-free polynucleotides, including cfDNA, can be extracted and isolated from bodily fluids through a partitioning step in which cell-free polynucleotides are separated from cells and other non-soluble components of the bodily fluid. Examples of partitioning techniques include use of binding resins or beads for example, or any other conventional technique. In some aspects, cells are not partitioned from cell-free polynucleotides first, but rather lysed. In some aspects, the genomic DNA of intact cells is partitioned through selective precipitation. Cell-free polynucleotides, including DNA, may remain soluble and may be separated from insoluble genomic DNA and extracted. According to some procedures, after addition of buffers and other wash steps specific to different kits, DNA may be precipitated using isopropanol precipitation. Further clean up steps may be used, such as binding resins, beads, or silica-based columns, to remove contaminants or salts. General steps may be optimized for specific applications. Non-specific bulk carrier polynucleotides, for example, may be added throughout the reaction to optimize certain aspects of the procedure such as yield.

In some aspects, cfDNA fragments are approximately uniform in length. In some aspects, cfDNA fragments are not approximately uniform in length. In some aspects, cfDNA fragments have an average length from about 50 to 1000 nucleotides in length. In some aspects, cfDNA fragments have an average length from about 50 to 500 nucleotides in length. In some aspects, cfDNA fragments have an average length from about 50 to 250 nucleotides in length. In some aspects, cfDNA fragments have an average length from about 50 to 200 nucleotides in length. In some aspects, cfDNA fragments have an average length from about 50 to 100 nucleotides in length. In some aspects, DNA fragments have an average length from about 100 to 300 nucleotides.

In an aspect, the disclosure provides a CENA standard which includes a plurality of synthetic polynucleotides derived from and/or representing one or more genomic polynucleotides including one or more sequence variants. Individual members of the plurality of synthetic polynucleotides have a 5' terminal and a 3' terminal end. In some aspects, synthetic polynucleotides of the standard include a molecular tag, such as a barcode sequence so that the synthetic polynucleotides can be distinguished from CFNA present in a test sample. In some aspects, at least a subset of the plurality of synthetic polynucleotides have a length ranging from about 100-300 bases.

The term "genomic polynucleotide," as used herein, refers to a polynucleotide derived or isolated from a chromosome. A genomic polynucleotide may refer to a contiguous portion of a chromosome of any length.

Fragment sizes of in vivo cfDNA are generally centered around about 140, 141, 142, 143, 144, 145, 146, 147, 148, 149, 150, 151, 152, 153, 154, 155, 156, 157, 158, 159, or 160 to 180 base pairs, approximately the length of DNA wrapped around a nucleosome plus its linker. Synthetic polynucleotides of a CENA standard disclosed herein may have a size distribution similar to that of in vivo cfDNA. In some aspects, at least a subset of the synthetic polynucleotides have a length ranging from about 100-300 bases. For example, at least 30% (e.g., at least 35%, 40%, 45%, 50%, 55%, 60%, 65%, 70%, 75%, 80%, 85%, 90%, 95% or greater than 95%) of the synthetic polynucleotides of a standard disclosed herein have a length ranging from about 100-300 bases. In some aspects, a majority of the synthetic polynucleotides of a standard disclosed herein have a length of about 100-300 bases. For example, at least 50% (e.g., at least 55%, 60%, 65%, 70%, 75%, 80%, 85%, 90%, 95% or greater than 95%) of the synthetic polynucleotides of a standard disclosed herein have a length ranging from about 100-300 bases.

It will be appreciated that depending on the source/type of nucleic acid, e.g., genomic or cell-free, being analyzed in a given assay, the size of synthetic polynucleotide may vary. For example, synthetic polynucleotides of a nucleic acid standard used in an assay for analyzing genomic DNA may have a length ranging from about 50 to 500, 1,000, 10,000 or more bases. As such, aspects of the present disclosure describing a CFNA standard are applicable to a nucleic acid standard with synthetic polynucleotides having a greater length than those of the CFNA standard.

As discussed herein, synthetic polynucleotides of a standard of the invention may be associated with a genomic polynucleotide sequence having a sequence variant. In some aspects, a standard includes synthetic polynucleotides that represent at least one subset of genomic polynucleotides (e.g., at least 2, 3, 4, 5, 6, 7, 8, 9, or 10 subsets). A CFNA standard provided herein can include at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 subsets.

A CENA standard disclosed herein may include a mixture of nucleic acids that are representative of certain in vivo CFNA samples, for example samples including a mixture of nucleic acids from normal, healthy cells of a subject and/or nucleic acids derived from cells associated with a disease or disorder, nucleic acids derived from a subject having drug resistance, nucleic acids derived from tumor cells, nucleic acids derived from fetal cells, nucleic acids derived from a non-autologous source (e.g., cell or tissue transplant), and/or nucleic acids derived from a pathogenic or non-pathogenic microorganism (e.g., bacteria or virus).

In some aspects of such standards, one or more synthetic polynucleotides including one or more mutant alleles and/or sequence variants is used to develop a CENA assay, validate aCFNA assay, optimize a CFNA assay, and/or evaluate the performance of a CFNA assay. In some aspects, detection of the one or more synthetic polynucleotides is used to validate, verify, and/or normalize the results obtained from a CFNA assay. In some aspects, a CFNA assay may be evaluated for its ability to detect the presence of the synthetic polynucleotide in a sample. This ability to detect the presence of a synthetic polynucleotide in a CENA standard may be representative of the assay's ability to detect a target nucleic acid in a CFNA sample.

In some aspects, a CFNA standard disclosed herein is useful for developing a CFNA assay, validating a CFNA assay, optimizing a CFNA assay, and/or evaluating the performance of a CENA assay, for example a CFNA assay to detect disease associated nucleic acids including tumor nucleic acids, fetal nucleic acids, non-autologous nucleic acids of transplanted cells, and/or pathogenic nucleic acids. In some aspects, a CFNA standard disclosed herein is useful to validate, verify, and/or normalize the results obtained from a CFNA assay.

The synthetic samples described herein have several key advantages over traditional cell-line, clinically derived and synthetic amplicon-based materials.

In various aspects, polynucleotides of the synthetic sample have a molecular tag incorporated into each synthetic polynucleotide fragment to distinguish contrived variants from clinical samples. The synthetic samples of the disclosure have the potential to include a large number of clinically relevant and genome-wide alterations which allows for the simultaneous analytical validation of targeted exons in a genetic assay, such as a comprehensive NGS assay.

In various aspects, a CFNA standard of the invention is a synthetic cfDNA sample. Due to the large number of high-purity, high frequency variants present in the synthetic cfDNA sample, there is a potential for cross-contamination to occur within a clinical or research setting. To mitigate the risk of trace amounts of synthetic cfDNA sample of impacting assay development activities, a molecular tag has been designed into the sequence of each variant containing synthetic polynucleotide as shown in FIG. 1. In various aspects, a barcode sequence includes at the 3' and 5' ends of each synthetic DNA molecule. The presence of this barcode sequence is positioned in such a way as to be non-overlapping with barcode sequences on adjacent synthetic DNA molecules in both position and sequence composition. Post-sequencing, these barcode sequences are filtered out during normal analysis but remain present in the data as a method to distinguish synthetic DNA fragments of the standard from DNA of clinical or cell line origin. This feature of the design is an advantage over traditional contrived sample models as a contamination event with these synthetic materials is readily detectable down to extremely low levels due to the presence of a barcode sequence on every synthetic DNA molecule.

As discussed herein, the fragmentation profile of the synthetic polynucleotides of the present disclosure can be precisely tailored to mimic the cfDNA fragmentation profile observed in clinical cases.

Figure 2:
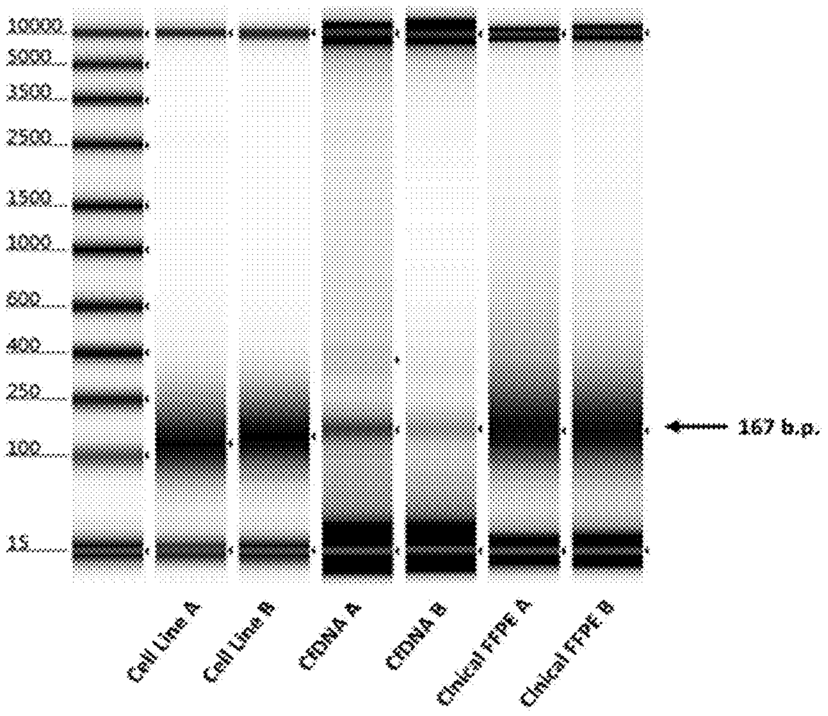
FIG. 2 is an image showing the size of DNA fragments from contrived samples and DNA from formalin-fixed paraffin-embedded (FFPE) clinical samples.

Clinical cfDNA samples contain fragmented double-stranded DNA sequences approximately 167 bp in length with a diverse range of start and end positions for any given position across the genome. Established methods for the creation of contrived samples from cell line, fresh frozen or FFPE clinical samples involve shearing of genomic DNA to the approximate length through sonication or enzymatic digestion. The fragmentation profile of contrived samples differs from cfDNA as the shearing methods used lack the resolution to create the uniform fragments. DNA fragmentation lengths of contrived samples range from ~100 bp to ~ 250 bp rather than the more narrow distribution centered around 167 bp profile of cfDNA. FIG. 2 illustrates the differences in fragmentation profiles between cfDNA and sheared cell line and clinical FFPE cases.

Using DNA manufacturing techniques, the lengths of each synthetic polynucleotide fragment can be precisely controlled to the pre-specified fragmentation length of clinical cfDNA specimens.

High-sensitivity NGS assays rely on both endogenous and exogenous molecular barcodes to create error-corrected distinct coverage which is utilized to positively identify mutations and eliminate false-positive variants. Endogenous Distinct Coverage (EDC) is described as distinct sequenced molecules spanning a variant which is represented by the start and end of the fragment alignment and the orientation of the alignment. Given the importance of EDC to the sensitivity of an NGS assays, it is necessary to create a contrived synthetic sample with a diverse range of start and end positions for a given Region of Interest (ROI) to allow for the accurate detection of targeted variants.

Figure 3:
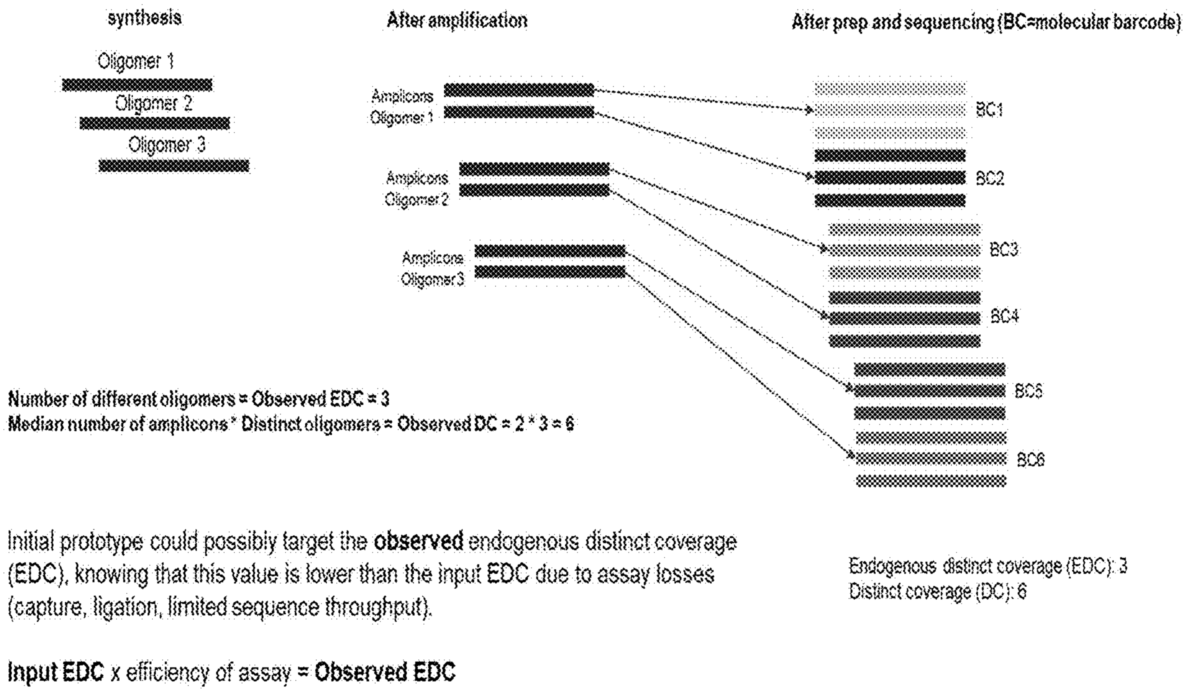
FIG. 3 is a schematic illustrating how specific DNA fragments or synthesized polynucleotides are represented by endogenous and exogenous barcodes in post sequencing NGS data.

FIG. 3 details how synthetic polynucleotides and amplicons are represented by total coverage and EDC in NGS data, in one aspect of the invention. In FIG. 3, synthetic DNA fragments or synthesized polynucleotides are represented by endogenous and exogenous barcode sequences in post sequencing NGS data. As illustrated in FIG. 3, three DNA fragments covering a specific ROI are represented. Each oligomer has a specific start and end position or endogenous barcode. If it were possible to sequence these oligomers in their native state, the total observed coverage and the EDC would both be calculated as 3×, a value which represents the three original oligomers covering the ROI. After PCR amplification, double-stranded amplicons are created from the original oligomers. These amplicons contain six DNA fragments representing the target ROI, however, the reverse strand of the amplicon maintains the same endogenous barcode sequence of the original oligomers. If it were possible to sequence these amplicons, the total coverage of the ROI would be 6× while the EDC would remain at 3×. EDC is described as the distinct molecules spanning the variant represented by fragments tagged with a specific unique molecular barcode sequence. During NGS library preparation each DNA fragment is tagged with a specific exogenous barcode sequence (represented above by color coded fragments above). In this example, each DNA strand is amplified to create 3×DNA copies. Sequencing this prepared NGS library would determine a total coverage of 18×, a Distinct Coverage (DC; as calculated by the exogenous barcode sequence) of 6× and an EDC of 3× for the ROI.

A key question addressed in the design of the synthetic samples of the invention was how to position the synthetic mutant/variant DNA molecules in a manner which would mimic the fragmentation profile (and therefore the endogenous coverage) observed in clinical cfDNA samples. If a contrived sample with only a single oligonucleotide fragment targeting each variant of interest was designed, the sample would not be representative of the cfDNA signature observed in clinical cases and it would not be possible to utilize EDC to call the targeted variant. In one aspect, to address this problem multiple mutation containing synthetic DNA fragments were synthesized with a consistent approximate fragment length of ~167 bp with distinct start and end positions upstream and downstream of the targeted variant position.

Figure 4:
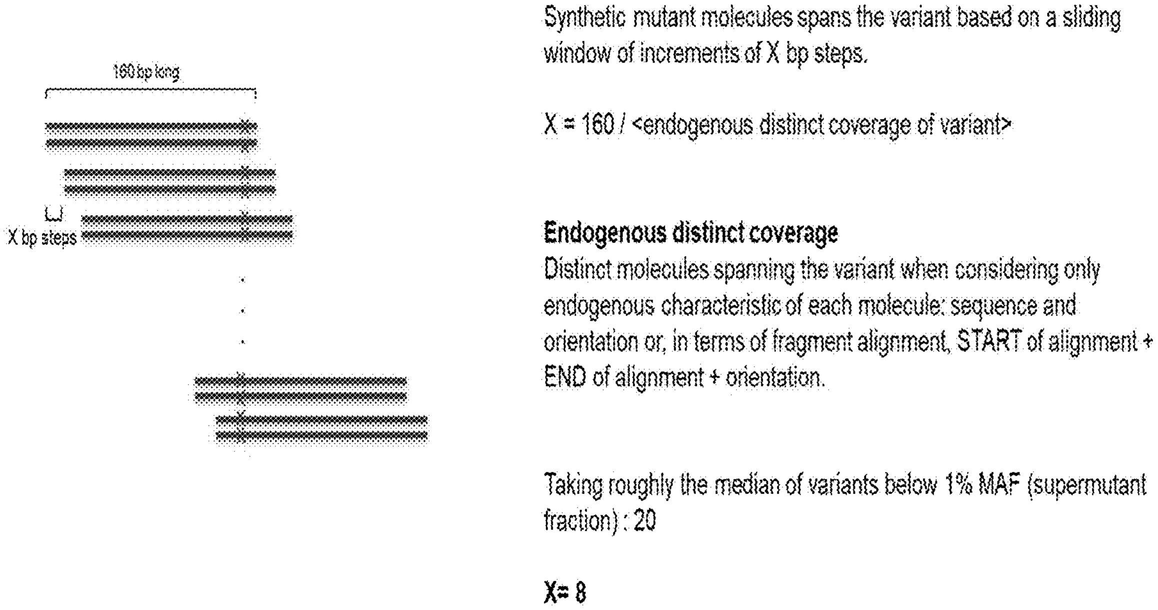
FIG. 4 is a schematic illustrating the design of synthetic cfDNA fragments targeting both single nucleotide variants (SNVs) and insertion/deletion (INDELS) events in one aspect of the invention.

To inform the positioning of the DNA fragments the endogenous molecular barcodes observed in 248 clinical samples were processed through PGDx elio Plasma Resolve™ assay. Using this data, it was determined that by creating a minimum of 20× synthetic mutant cfDNA fragments with start and end positions defined by a sliding window of 8 bp it was possible to mimic the distribution of endogenous barcodes observed in the clinical dataset (FIG. 4). FIG. 4 illustrates the design of the synthetic cfDNA fragments targeting both SNVs and INDELS, in one aspect of the invention. Although the initial proof-of-concept design uses an 8 bp sliding window and coverage of 20× fragments, other tiling window lengths and coverage depths may be used to balance synthetic cfDNA synthesis costs versus the desired number of alterations and how closely the contrived sample mimics clinical DNA.

In various aspects, the combination of multiple variants of SNV/INDEL translocations and amplifications into a single synthetic sample allows for simultaneous evaluation of each variant type. A key advantage in using synthetic oligomers to create contrived materials is that many hundreds of variants can be included in the design. The simplest variant type to include are SNV and INDELS as each fragment is simply synthesized with the point mutation or INDEL incorporated into the sequences (FIG. 4). In one aspect, the synthetic sample includes oligonucleotides useful in detection of SNVs and INDELS across 21 genes representing 480 target genomic regions. Bach target genomic region contains a single variant. 59 clinically actionable or hotspot variants were included along with 421 panel-wide variants. Table 1 below lists the genes of interest represented in the design in one aspect of the invention.

TABLE 1

Target Genes Containing SNVs and Indels.

| | | | | | | |
|---|---|---|---|---|---|---|
| FGFR1 | NTRK1 | RET | BRCA1 | ERBB2 | IDH2 | MET |
| FGFR2 | NTRK2 | ROS1 | BRCA2 | H3F3A | KIT | NRAS |
| FGFR3 | NTRK3 | BRAF | EGFR | IDH1 | KRAS | PDGFRA |

Figure 5:
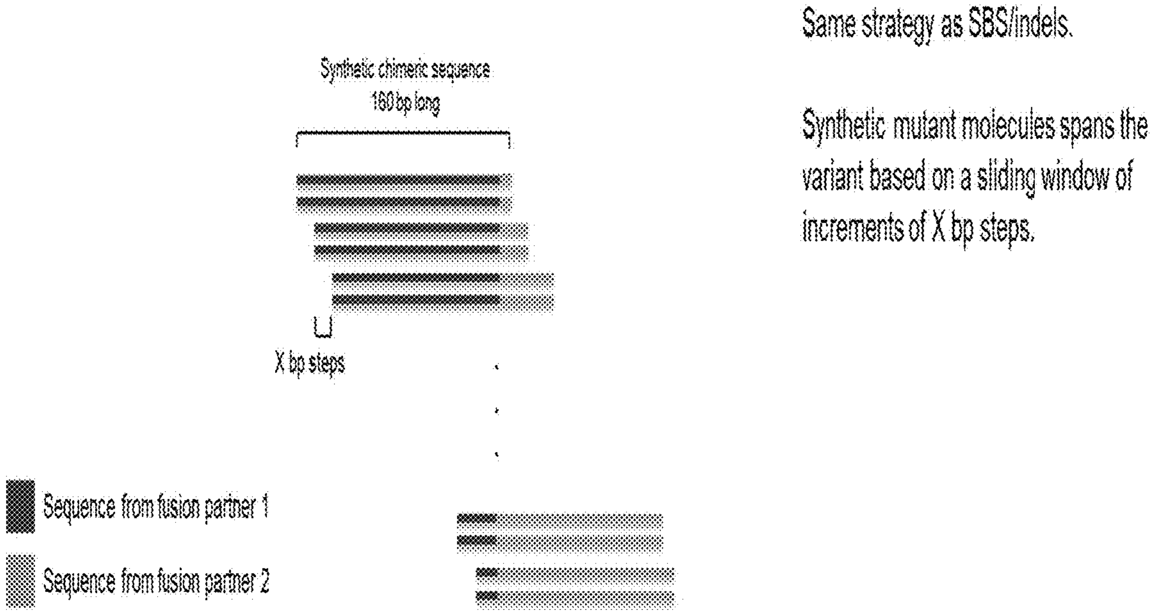
FIG. 5 is a schematic illustrating the design of synthetic chimeric cfDNA polynucleotides representing specific translocation variants of interest in one aspect of the invention.

Synthetic DNA fragments can also be used to mimic the break-point coverage of a translocation event where each molecule contains sequences from both fusion gene partners. The approach utilizes the same 8× bp sliding window and >20× fragment strategy described for SNVs and INDELS. FIG. 5 details how translocation variants are represented in the design. In one aspect, FIG. 5 illustrates the design of synthetic chimeric cfDNA sequences representing specific translocation variants of interest. In one aspect, 10 target translocation events of the invention are listed in Table 2.

TABLE 2

Target Translocation Genes.

| | |
|---|---|
| ALK | NTRK1 |
| BRAF | NTRK2 |
| FGFR1 | NTRK3 |
| FGFR2 | RET |
| FGFR3 | ROS1 |

Figure 6:
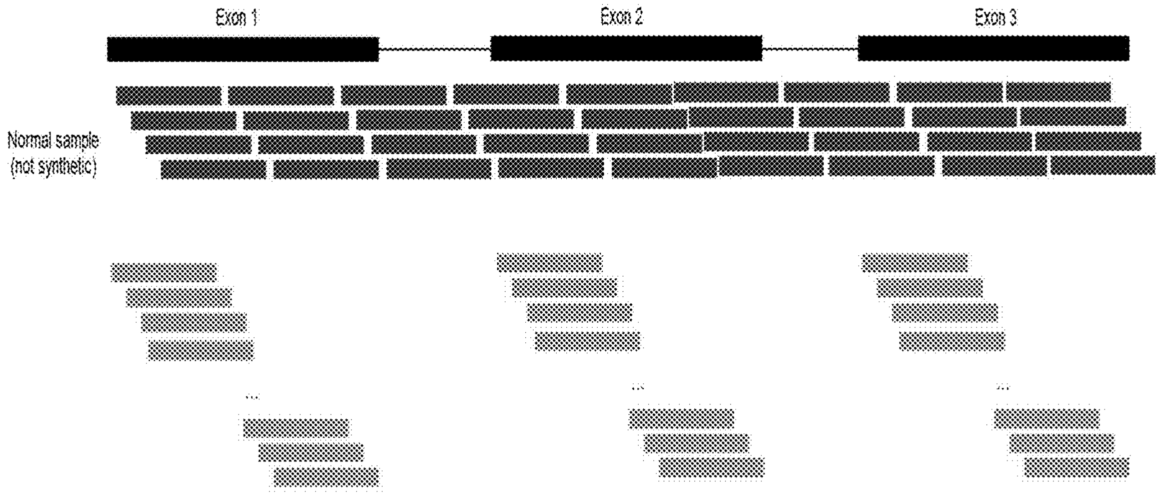
FIG. 6 is a schematic illustrating the design of synthetic DNA polynucleotides of copy number variants in one aspect of the invention.

Amplification events can also be included in design of synthetic materials. To create a synthetic CNV event, a separate panel of wild-type oligomers targeting the amplified gene may be synthesized (CNV Panel). Unlike SNVs/INDELS and translocations, CNVs do not require EDC or DC to make a positive call, however, a sliding window approach to the positioning of the oligonucleotides may also be implemented. The synthetic sequences are restricted to the coding exons of the target gene as coverage of the full length of the gene is unnecessary. The concentration of the synthesized CNV Panel may be normalized to the concentration of the main SNV/INDEL/translocation variant panel and combined in specific ratios to mimic the fold-change events observed in a clinical case. FIG. 6 details the increased concentration of synthetic wild-type sequences relative to the normal background. FIG. 6 illustrates the design of a synthetic copy number variant, in one aspect of the invention. The design does not include a synthetic amplification variant but is designed as to allow inclusion of an amplification in the ERBB2 gene without interfering with the SNV/INDEL or translocation calls already included in the design.

In various aspects, the invention allows control over the allele frequencies of the variants of interest. An essential part of the analytical validation of an NGS assay involves the establishment and confirmation of the limit-of detection (LOD) for specific variants. To establish an LOD, multiple dilution levels of a clinical or contrived sample containing the targeted variant of interest are created. Each dilution level targets a specific varient allele frequency (VAF) or copy number values above, at or below the anticipated LOD of the assay. These serial dilutions are processed through the assay multiple times to determine level at which the variant is no-longer detected within a given confidence interval (typically 99%).

When combining multiple cell-line or clinical samples containing variants of interest, the relative VAFs of each variant often differ within and across samples. Due to the differences in variant abundance, a serial dilution of the contrived sample will result in distinct variants reaching target dilution levels at different rates. Table 3 provides an example of this effect.

TABLE 3

| Dilution Series to Establish an LOD. | | | | | | |
|---|---|---|---|---|---|---|
| Cell Line | Variant | Initial Contrived Blend VAF | Level 1 | Level 2 | Level 3 | Level 4 |
| Cell Line A | EGFR T790M | 17% | 1.66% | 1.11% | 0.83% | 0.42% |
| Cell Line A | EGFR L858R | 8% | 0.75% | 0.50% | 0.38% | 0.19% |
| Cell Line A | NRAS G12V | 7% | 0.69% | 0.46% | 0.35% | 0.17% |
| Cell Line B | KRAS Q61L | 17% | 1.67% | 1.11% | 0.83% | 0.42% |
| Cell Line B | NRAS A146T | 3% | 0.31% | 0.21% | 0.16% | 0.08% |
| Cell Line C | NRAS Q61R | 3% | 0.30% | 0.20% | 0.15% | 0.08% |
| Cell Line C | EGFRG719S | 17% | 1.66% | 1.11% | 0.83% | 0.41% |

As shown in Table 3, three cell lines containing seven variants of interest are combined to create and initial contrived blend for the standard. This blend is further diluted to four levels, Level 1 above the anticipated LOD, Level 2 in between Level 1 and Level 3, Level 3 at the anticipated LOD of the assay, and Level 4 below the anticipated LOD of the assay. The differences in VAF levels across variants complicate the simultaneous establishment of an LOD for each of the variants in the blend.

Synthetic cfDNA samples overcome the limitations of combined cell lines or clinical cases as each oligonucleotide is synthesized to contain a single variant of interest. These oligonucleotides also have approximately equimolar concentrations which results in the variant panel containing 100% mutant molecules in equal abundance. To create a dilution series, the variant panel is first diluted with an equalized genome equivalent concentration of a wild-type background to create a working stock. The wild-type background DNA can be sourced from either synthetic DNA created in a similar manner to the variant panel or from a cell line or healthy normal donor sample. This working stock is further diluted with increasing ratios of wild-type DNA to create the desired target VAF levels.

Figure 7:
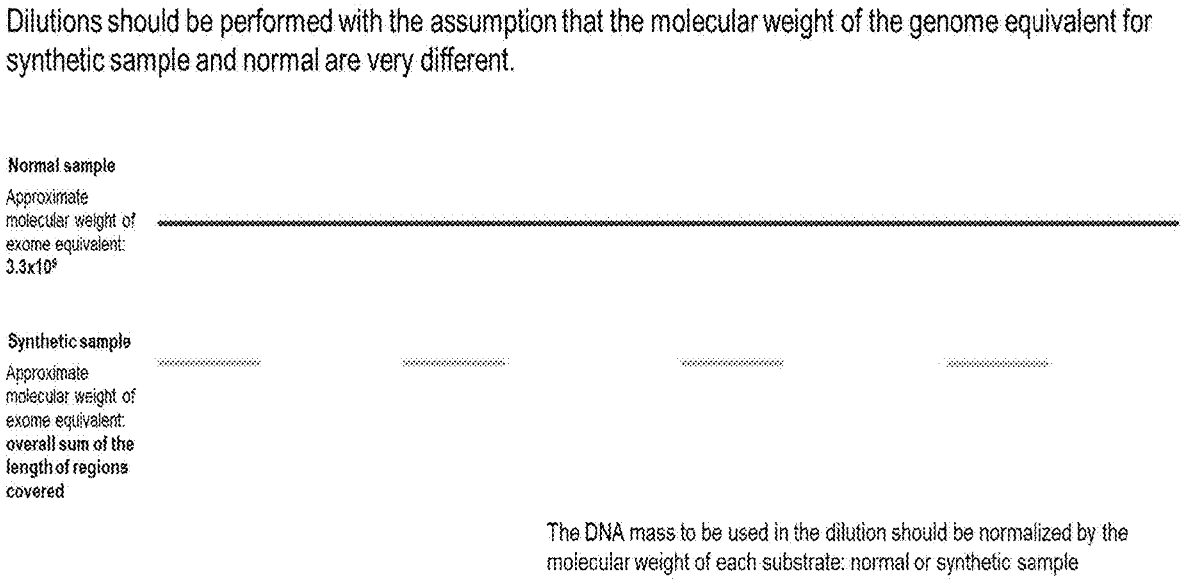
FIG. 7 is a schematic illustrating how an initial variant panel may be combined with wild-type DNA via dilution. Dilutions are performed with the assumption that the molecular weight of the genome equivalent for the synthetic sample and normal sample are very different.
Figure 8:
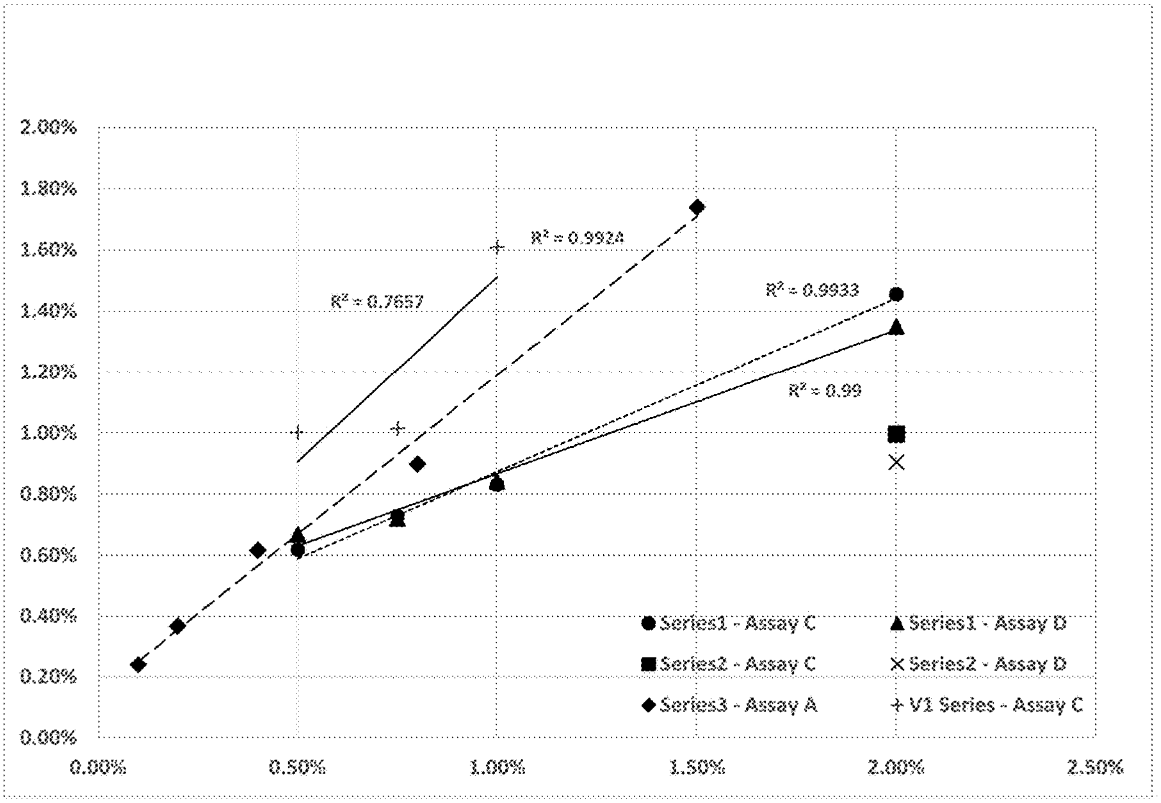
FIG. 8 shows dilution series linearity and assay comparison.

Table 4 illustrates the advantages of using these synthetic standards using variants across the FGFR1 gene as an example. Four dilution levels of the synthetic DNA were created targeting 10%, 2%, 1% and 0.5% VAF levels. These samples were sequenced in triplicate using a Hybrid-capture NGS assay targeting the 21 genes included in the variant panel. The average VAF for each diluted variant level closely matches the targeted values and the variability of the allele frequencies across variants is significantly lower than typically seen in cell line blends. In addition, a similar trend was observed across all 21 genes and 322 variants included in the proof-of-concept design. FIG. 7 shows how an initial variant panel may be combined with wild-type DNA.

TABLE 4

| []VAF levels of FGFR1 Dilution Series. | | | | |
|---|---|---|---|---|
| Variant | Target 10% VAF | Target 2% VAF | Target 1% VAF | Target 0.5% |
| FGFR1 A16S | 9.31% | 2.05% | 1.12% | 0.72% |
| FGFR1 A497V | 10.64% | 1.83% | 1.20% | 0.95% |
| FGFR1 A671V | 10.00% | 1.74% | 1.06% | Not Detected |
| FGFR1 E75D | 11.99% | 2.97% | 1.81% | 0.65% |
| FGFR1 F747C | 13.65% | 3.05% | 1.70% | Not Detected |
| FGFR1 G337W | 9.15% | 2.04% | 1.03% | Not Detected |
| FGFR1 I395F | 13.45% | 2.37% | 1.32% | Not Detected |
| FGFR1 K536N | 10.67% | 2.60% | 1.17% | Not Detected |
| FGFR1 P179S | 13.26% | 3.38% | 1.19% | 0.75% |
| FGFR1 P587S | 11.97% | 2.21% | 1.47% | 0.81% |
| FGFR1 S281C | 14.43% | 2.11% | 1.68% | 0.88% |

TABLE 4-continued

| []VAF levels of FGFR1 Dilution Series. | | | | |
|---|---|---|---|---|
| Variant | Target 10% VAF | Target 2% VAF | Target 1% VAF | Target 0.5% |
| FGFR1 S452R | 6.80% | 1.37% | 0.48% | 0.67% |
| FGFR1 S794F | 5.53% | 1.13% | Not Detected | Not Detected |
| FGFR1 V706L | 8.36% | 1.47% | 0.74% | Not Detected |
| FGFR1 Y228F | 13.60% | 2.54% | 1.12% | Not Detected |
| Average VAF | 10.85% | 2.19% | 1.22% | 0.78% |

Microsatellite instability (MSI) can also be included in design of synthetic materials. The mechanism of MSI generation is generally believed to be DNA slippage in the process of replication, or mismatch of the basic group of slippage strand and complementary strand in the process of DNA replication and repair, resulting in one or more of the repeating units being omitted or inserted. MSI has been useful in diagnosing certain subsets of cancer and tumors. Typically, regions with repeated sequence motifs of one or two bases are examined for somatic variation. The units are generally repeated about 5-40 times so that they are distinguishable within single sequence reads. The degree of variation in the repeat lengths within DNA samples provides an indication of the nature of the somatic variation. Accurate detection of such repetitive structures is often problematic as NGS systems can be challenged by such sequences with these difficulties varying depending on sequence context. Having a set of defined repeats can help distinguish artifactual technical variation from true biological variation and thus aid in identifying important biological readouts from individuals with disease or drug resistance.

As discussed herein, in some aspects, a CENA standard disclosed herein is useful for developing a CFNA assay, validating a CFNA assay, optimizing a CFNA assay, and/or evaluating the performance of a CENA assay. For example, a CENA standard may be useful in developing a CFNA assay by allowing adjustment of one or more assay conditions to improve at least one performance metric relative to at least one reference performance metric.

In some aspects, at least one performance metric is a detection rate (observed abundance/expected abundance) or a LOD. In some aspects, the assay includes an amplification reaction. In some aspects, an assay condition is an amplification temperature, length of an amplification step, or number of amplification cycles.

The term "observed abundance," as used herein, generally refers to the relative representation of, for example, a particular species (e.g., target nucleic acid) in a sample (e.g., nucleic acid sample) that is observed, detected, or measured. For example, an observed abundance may refer to the relative representation of a target polynucleotide in a polynucleotide sample that is observed or detected, for example by an assay such as a cell-free nucleic acid assay (CFNA assay). This may be, for example, the number of target polynucleotide molecules relative to the total number of polynucleotides of the polynucleotide sample. If the target polynucleotide includes a mutant allele or variant allele, an observed abundance may refer to the observed, detected or measured allelic frequency of the mutant in a sample. Abundance may be described as a fraction or percentage, for example of the total or a subset of the total (e.g., variant allele relative to all alleles, including wild-type and other mutants, present in a sample). An abundance may, in some cases, be described as a concentration including, but not limited to, mass concentration, molar concentration, number concentration, and volume concentration, or other acceptable unit of measure.

The term "expected abundance," as used herein, generally refers to the relative representation of, for example, a particular species (e.g., target nucleic acid) in a sample (e.g., nucleic acid sample) that is expected to be characteristic of the sample. For example, an expected abundance may refer to the relative representation of a target polynucleotide in a polynucleotide sample that is expected to be characteristic of the sample (e.g., a reference sample or standard sample). The relative representation of a target polynucleotide in a polynucleotide sample may be expected, for example, if the sample was artificially generated by spiking in or adding known amounts of a target polynucleotide to a polynucleotide sample (the amounts are also known). Abundance may be described as a fraction or percentage, for example of the total (e.g., number of target polynucleotide molecules relative to total number of polynucleotide molecules in the sample) or a subset of the total (e.g., number of molecules of a mutant allele relative to the total number of molecules of the gene, including mutant and wild-type alleles). Abundance may, in some cases, be described as a concentration including, but not limited to, mass concentration, molar concentration, number concentration, and volume concentration, or other acceptable unit of measure.

The term "estimated abundance," as used herein, generally refers to an estimate of the relative representation of, for example, a particular species (e.g., target nucleic acid) in a sample (e.g., cell-free nucleic acid sample). An estimated abundance may be a value obtained from adjusting an observed abundance by a calibration or correction scheme which accounts for variability or error in a measurement method and/or system. Where a measurement method or system has little variability and/or error and is highly sensitive, specific, and/or accurate, an estimated abundance and an observed abundance may deviate insignificantly. Where a measurement method or system has high variability and/or low sensitivity, specificity, and/or accuracy, an estimated abundance and an observed abundance may differ significantly. Abundance may be described as a fraction or percentage, for example of the total (e.g., number of target polynucleotide molecules relative to total number of polynucleotide molecules) or a subset of the total (e.g., number of molecules of a mutant allele relative to the total number of molecules of the gene, including mutant and wild-type alleles). Abundance may, in some cases, be described as a concentration including, but not limited to, mass concentration, molar concentration, number concentration, and volume concentration, or other acceptable unit of measure.

In some aspects, the observed abundance of the target nucleic acid is determined by an amplification reaction, such as digital polymerase chain reaction (dPCR), droplet digital polymerase chain reaction (ddPCR), or quantitative polymerase chain reaction (qPCR). An amplification reaction (e.g., dPCR, ddPCR, or qPCR) may be performed with amplification primers specific to the target nucleic acid. For example, primers may be allele specific primers if a target nucleic acid is a mutant allele.

In some aspects, the observed abundance of the target nucleic acid present in the CENA sample is determined by (a) sequencing a plurality of amplification products to generate a plurality of sequence reads, wherein the plurality of amplification products are generated by amplifying the target nucleic acid and non-target nucleic acids of the CFNA sample; and (b) analyzing the sequence reads to calculate the observed abundance of the target nucleic acid.

Amplifying target nucleic acids and non-target nucleic acids may be used to increase the amount of material available for analysis, for example sequencing analysis, if the amount of starting material is low and/or insufficient to, e.g., assess copy number of the target nucleic acid.

In one aspect, a CFNA standard disclosed herein may be useful in determining the detection limit of an assay, for example a CENA assay involving an instrument (e.g., a dPCR machine, a ddPCR machine, a qPCR machine, an NGS machine, and the like) or specific method (e.g., a method including steps of nucleic acid extraction, purification, ligation, amplification, digestion, and the like). The assay may be performed, for example, with a plurality of CFNA standards, each of which has a synthetic polynucleotide at an expected abundance and, collectively. For each standard, the observed abundance of the synthetic polynucleotide may be compared to an observed abundance of a sample containing no nucleic acid (e.g., a background measurement or noise level) to determine the expected abundance at which the observed abundance of the synthetic polynucleotide from the standard is indistinguishable from the background measurement.

In one aspect, a CFNA standard disclosed herein may be useful in determining the detection limit of an assay, for example a CENA assay involving an instrument (e.g., a dPCR machine, a ddPCR machine, a qPCR machine, an NGS machine, and the like) or specific method (e.g., a method including steps of nucleic acid extraction, purification, ligation, amplification, digestion, and the like). The assay may be performed, for example, with a single CFNA standard having a plurality of unique synthetic polynucleotides (e.g., each of the synthetic polynucleotides is independently identifiable, for example by amplification and/or sequencing of a molecular tag, such as a barcode sequence). A single CENA standard may include at least 2 synthetic polynucleotides (e.g., at least 3, 4, 5, 6, 7, 8, 9, 10 or greater than 10 synthetic polynucleotides). Each of the synthetic polynucleotides present in the CFNA standard may be present in the standard at about the same expected abundance. In some aspects, each synthetic polynucleotide of the CFNA standard includes a mutant allele. Where each synthetic polynucleotide of the CFNA standard includes a mutant allele, the expected abundance of the synthetic polynucleotide may be an allelic frequency of less than about 50%, 40%, 30%, 20%, 10%, 5%, 1%, 0.5%, 0.1%, 0.01%, or 0.001%. Synthetic polynucleotides in the lower MAF range of <10% may preferably be used in limit of detection studies. Synthetic polynucleotides with higher abundance in the MAF range of 20%-50% may preferably be used in testing carryover contamination of nearby samples during processing and assessing assay ability of germline level MAF detection and reporting.

In one embodiment, the invention further provides a system for estimating abundance of a target nucleic acid including a sequence variant in a CFNA sample including a target nucleic acid and non-target nucleic acids. The system includes a quantification module configured to determine copy number of the target nucleic acid in the CFNA sample to yield an observed abundance of the target nucleic acid; and a computer module having functionality to determine an estimated abundance of the target nucleic acid in the CFNA sample by adjusting the observed abundance of the target nucleic acid using the observed abundance of the standard. In some aspects, the system further includes a report generator that sends a report to a recipient, wherein the report contains at least one of the following: observed abundance of the target nucleic acid, estimated abundance of the target nucleic acid, observed abundance of the synthetic polynucleotide, and expected abundance of the synthetic polynucleotide.

In an aspect, the invention further provides a kit including cell-free nucleic acid (CFNA) standard of the disclosure, and optionally one or more one or more reagents for conducting a CFNA assay and/or user instructions for using the standard in a CFNA analysis.

In various aspects of the invention described herein, the copy number of a target nucleic acid in a cell-free nucleic acid sample or a synthetic polynucleotide in a standard is determined to obtain an observed abundance. The copy number or number of molecules may be determined using various suitable methods including, but not limited to, digital PCR (dPCR), droplet digital (ddPCR), quantitative PCR, and NGS methods.

NGS techniques allow for the determination of nucleotide sequences in a highly parallel fashion. Nucleic acid amplification and NGS techniques include, but are not limited to, single-molecule real-time sequencing, ion semiconductor sequencing, pyrosequencing, sequencing by synthesis (SBS), sequencing by ligation (SBL), chain termination sequencing, massively parallel signature sequencing, polony sequencing, DNA nanoball sequencing, Heliscope single molecule sequencing, nanopore DNA sequencing, sequencing by hybridization, sequencing by mass spectrometry, microfluidic Sanger sequencing, and microscopy-based sequencing techniques.

Types of templates that can be used for NGS reactions include clonally amplified templates originating from single DNA molecules and single DNA molecule templates. Methods for preparing clonally amplified templates include emulsion PCR (emPCR) and solid-phase amplification. Other methods for preparing clonally amplified templates include Multiple Displacement Amplification (MDA), wherein random hexamer primers are annealed to a template and DNA is synthesized by a high fidelity enzyme, such as typically phi29, at a constant temperature or near constant temperature.

Single-molecule templates are another type of template that can be used for NGS reactions. Spatially separated single molecule templates can be immobilized on solid supports by various methods. In one approach, individual primer molecules are covalently attached to the solid support. Adaptors are added to the templates, and the templates are then hybridized to the immobilized primers. In another approach, single molecule templates are covalently attached to the solid support by priming and extending single-stranded, single molecule templates from immobilized primers. Universal primers can then be hybridized to the templates. In yet another approach, single polymerase molecules are attached to the solid support, to which primed templates are bound.

Following template preparation, sequencing can be performed. Exemplary sequencing and imaging methods for NGS include, but are not limited to, cyclic reversible termination (CRT), sequencing by ligation (SBL), single-molecule addition (e.g., pyrosequencing), and real-time sequencing. Other sequencing methods for NGS include, but are not limited to, nanopore sequencing, sequencing by hybridization, nano-transistor array based sequencing, polony sequencing, scanning tunneling microscopy (STM) based sequencing, and nanowire-molecule sensor based sequencing. Double-ended sequencing methods can also be used for NGS.

Illustrative examples of the invention are provided in the working examples and further illustrate the advantages and features of the present invention, but are not intended to limit the scope of the invention. While these example are typical of those that might be used, other procedures, methodologies, or techniques known to those skilled in the art may alternatively be used.

Synthetic cfDNA sample creation (v1 and v2). Proof-of-concept synthetic cfDNA material (v1) was manufactured and used to develop a dilution methodology, assess functionality as a sample in PGDx hybrid capture assays and ddPCR, and evaluate sequencing and individual variant performance metrics. Recommendations based on this proof-of-concept data were presented and incorporated into an updated version of synthetic cfDNA material (v2) with process modifications to improve equal representation of DNA fragments across the simulated variants and consistency in fragment lengths.

A total of 27 contrived samples, synthetic cfDNA blended with wildtype (WT) DNA were created (Table 5). Over 120 replicates of the synthetic cfDNA contrived samples were run in four PGDx plasma assays, Assay A-D, for feasibility studies and 2 verification studies. All assays utilize hybrid capture library preparation and NGS sequencing methodologies but vary in either target gene panel (size and variants), or small variations on library chemistry for each sequencer, as shown in Table 5.

TABLE 5

Assay variations in target gene panel size and sequencer.

| Assay | Genes | Sequencer |
|---|---|---|
| A | 33 | NEXTSEQ ® |
| B | 27 | NEXTSEQ ® |
| C | 33 | NEXTSEQ ® |
| D | 521 | NOVASEQ ® |

Sample Creation: the synthetic cfDNA material (both v1 and v2) was acquired as 100 ng of lyophilized product in a single cryotube. The material was resuspended in 20 μl of EB to create a 5 ng/ul stock and assumed to have 100% variant allele frequencies (VAF) for all variants. The synthetic design of the material made the use of fluorometric quantitation unreliable due to size and MW differences compared to gDNA. To standardize inputs dilutions were based on copies per microliter. The copies per ul were calculated for 160 bp DNA fragment (650 g/mol) in the stock solution of 5 ng/ul and divided by the total number of sites (332 targeted mutations) to estimate the total copies/site/ul in the stock solution. This stock (87145626 copies/ul) was serially diluted to 1000 copies/ul working stock. Multiple VAF levels were targeted by blending this working stock of synthetic cfDNA at 100% VAF with sheared genomic wild type (WT) DNA from cell lines also diluted to 1000 copies/ul (~3.56 ng/ul) based on volumes.

Synthetic cfDNA sample blended with WT DNA to targeted VAFs were run through internal PGDx plasma hybrid capture assay sequenced via an NGS system (ILLUMINA®'s NEXTSEQ® sequencer or NOVASEQ® sequencer). Sheared WT cell line DNA or normal plasma cfDNA was used as background WT DNA for blending to the desired VAFs.

TABLE 6

Synthetic cfDNA Contrived Sample summary.

| Sample | Study Type | Targeted VAF | Design Version | NGS Replicates | Assay |
|---|---|---|---|---|---|
| 5624 | Feasibility | 50% | V1 | 0 | |
| 5625 | Feasibility | 10% | V1 | 1 | B |
| 5627 | Feasibility | 2% | V1 | 1 | B |
| 5628 | Feasibility | 1% | V1 | 1 | B |
| 5629 | Feasibility | 0.50% | V1 | 1 | B |
| 5635 | Feasibility | 10% | V1 | 0 | |
| 5636 | Feasibility | 2% | V1 | 0 | |
| 5637 | Feasibility | 1% | V1 | 2 | C |
| 5638 | Feasibility | 0.75% | V1 | 3 | C |
| 5639 | Feasibility | 0.50% | V1 | 2 | C |
| 5725 | Feasibility | 50% | V2 | 0 | |
| 5726 | Feasibility | 10% | V2 | 0 | |
| 5727 | Feasibility/ Verification | 2% | V2 | 6 | B, C, D |
| 5728 | Feasibility/ Verification | 1% | V2 | 19 | B, C, D |
| 5729 | Feasibility/ Verification | 0.75% | V2 | 19 | B, C, D |
| 5730 | Feasibility | 0.5% | V2 | 15 | C, D |
| 5740 | Feasibility | 50% | V2 | 0 | |
| 5741 | Verification | 10% | V2 | 0 | |
| 5742 | Verification | 2% | V2 | 21 | C, D |
| 5743 | Verification | 1% | V2 | 0 | |
| 5744 | Verification | 0.75% | V2 | 0 | |
| 5821 | Feasibility | 5.00% (NP WT) | V2 | 2 | A |
| 5823 | Feasibility | 1.50% (NP WT) | V2 | 5 | A |
| 5824 | Feasibility | 0.80% (NP WT) | V2 | 5 | A |
| 5825 | Feasibility | 0.40% (NP WT) | V2 | 5 | A |
| 5826 | Feasibility | 0.20% (NP WT) | V2 | 5 | A |
| 5827 | Feasibility | 0.10% (NP WT) | V2 | 5 | A |

With synthetic cfDNA v1, single replicates at targeted MAFs 0.5%-10% were run in assay B and approximately 80% of the expected SNV mutations were identified in the higher targeted MAF contrived samples. All pre-filter files were examined and 97% of the SNV variants were identified in the upstream files (Table 6). All 5 of the expected translocations were detected above 1% targeted MAF (Table 7).

TABLE 7

Assay B Synthetic cfDNA v1 SNV/Indel performance summary.

| Sample | Target MAF | Expected SNV's | Observed SNV's | % Variant Identified | Average MAF % (Called) | % Variants Identified (Upstream Files) | Average MAF % (Upstream Files) | False Positives |
|---|---|---|---|---|---|---|---|---|
| 5625 | 10% | 322 | 279 | 86.6% | 9.37% | 314 | 9.20% | 6 |
| 5627 | 2% | 322 | 277 | 86.0% | 1.84% | 314 | 1.81% | 1 |
| 5628 | 1% | 322 | 254 | 78.9% | 0.99% | 312 | 0.92% | 0 |
| 5629 | 0.50% | 322 | 105 | 32.6% | 0.72% | 312 | 0.46% | 1 |

TABLE 8

Assay B Synthetic cfDNA v1 Translocation performance summary.

| Sample | Target MAF | Expected Translocations | Observed Translocations | % Identified |
|---|---|---|---|---|
| 5625 | 10% | 5 | 5 | 100% |
| 5627 | 2% | 5 | 5 | 100% |
| 5628 | 1% | 5 | 5 | 100% |
| 5629 | 0.50% | 5 | 2 | 40% |
| 5727 | 2% | 5 | 5 | 100% |
| 5728 | 1% | 5 | 4 | 80% |
| 5729 | 0.75% | 5 | 4 | 80% |

A second dilution V1 series targeting 0.5%-1% MAF (Table 8) was created and prequalified in Assay C for use in verifications studies of Assay B. Prequalification results from Assay C detected 51-84% of expected SNVs.

TABLE 9

[]Assay C Synthetic cfDNA v1 SNV/Indel performance summary.

| Sample | Target MAF | Expected SNVs | Observed SNVs | % Variants Identified | Average MAF % (called) |
|---|---|---|---|---|---|
| 5637* | 1.00% | 271 | 188* | 69% | 1.61% |
| 5638 | 0.75% | 271 | 229 | 84% | 1.02% |
| 5639* | 0.50% | 271 | 179* | 51% | 0.98% |

*5637 and 5639 each had a low replicate.

The synthetic cfDNA v2 was used to create 4 dilutions series used in multiple studies. SNV metrics for v2 contrived samples are listed in Table 9 including assay and replicates.

TABLE 10

Synthetic cfDNA v2 SNV/Indel performance summary in assay A, C, D.

| Sample | Target MAF | SNVs in Panel | Observed SNVs | % Variants Identified in Level | Replicates | Assay | Average MAF % (called) |
|---|---|---|---|---|---|---|---|
| 5727 | 2.00% | 322 | 287 | 89% | 3 | B | 1.97% |
| 5728 | 1.00% | 322 | 280 | 87% | 3 | B | 1.1% |
| 5729 | 0.75% | 322 | 212 | 66% | 3 | B | 0.67% |
| 5727 | 2.00% | 307 | 268 | 87% | 2 | C | 1.46% |
| 5728 | 1.00% | 307 | 213 | 69% | 2 | C | 0.83% |
| 5729 | 0.75% | 307 | 154 | 50% | 2 | C | 0.73% |
| 5730 | 0.50% | 307 | 71 | 23% | 2 | C | 0.62% |
| 5742 | 2.00% | 307 | 191 | 62% | 2 | C | 1.00% |
| 5727 | 2.00% | 322 | 282 | 88% | 4 | D | 1.35% |
| 5728 | 1.00% | 322 | 218 | 68% | 17 | D | 0.84% |
| 5729 | 0.75% | 322 | 151 | 47% | 17 | D | 0.72% |
| 5730 | 0.50% | 322 | 77 | 24% | 13 | D | 0.67% |
| 5742 | 2.00% | 322 | 248 | 77% | 4 | D | 0.91% |
| 5821 | 5.00% | 307 | 270 | 88% | 2 | A | 0.14% |
| 5823 | 1.50% | 307 | 230 | 75% | 5 | A | 1.74% |
| 5824 | 0.80% | 307 | 74 | 24% | 5 | A | 0.90% |
| 5825 | 0.40% | 307 | 74 | 24% | 5 | A | 0.62% |
| 5826 | 0.20% | 307 | 12 | 4% | 5 | A | 0.37% |
| 5827 | 0.10% | 307 | 4.2 | 1% | 5 | A | 0.24% |

Figure 9:
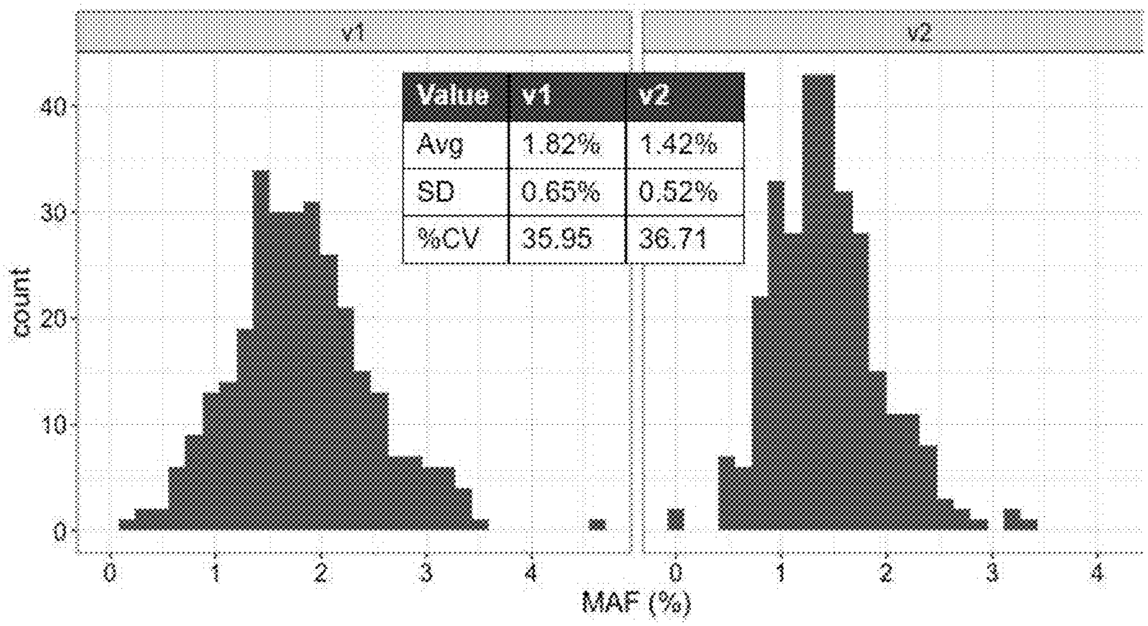
FIG. 9 shows distribution of allele frequencies in synthetic cfDNA V1 vs. V2. V2 shows reduced variability around a targeted mutant allele frequency ("MAF").
Figure 10:
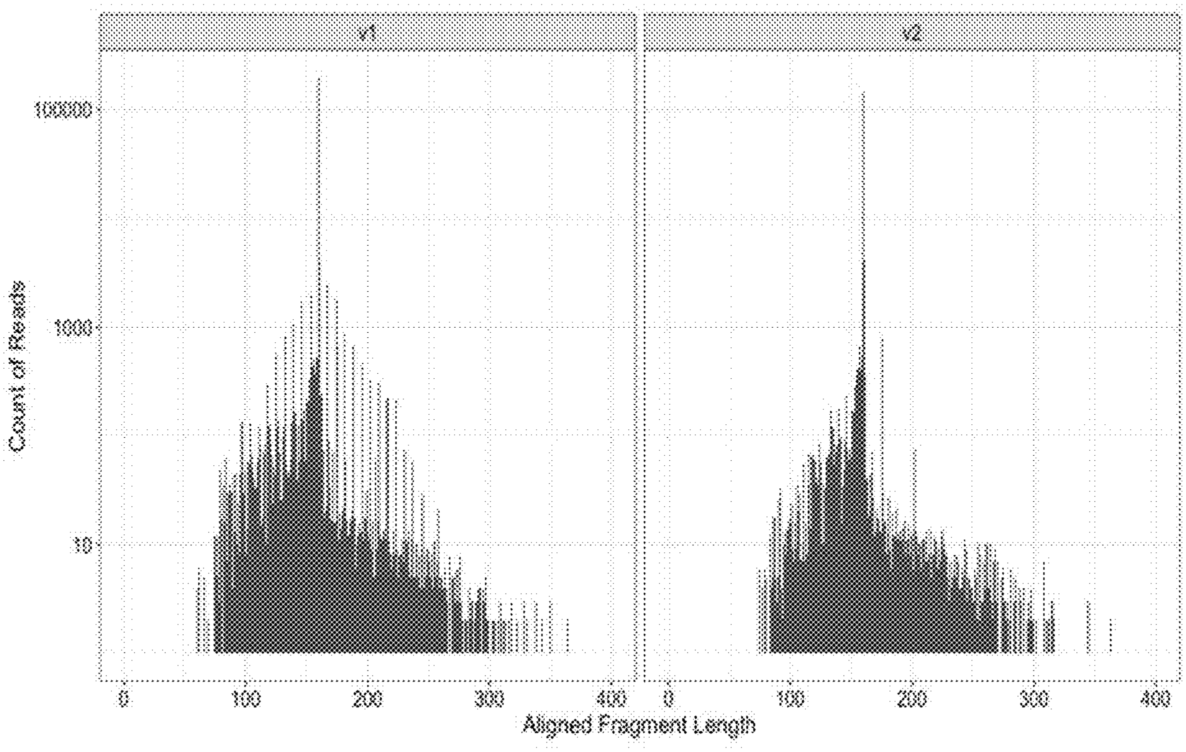
FIG. 10 shows distribution of sequence fragment lengths from estimated 2% synthetic cfDNA+WT cell line DNA contrived sample in v1 and v2 of the design.
Figure 11:
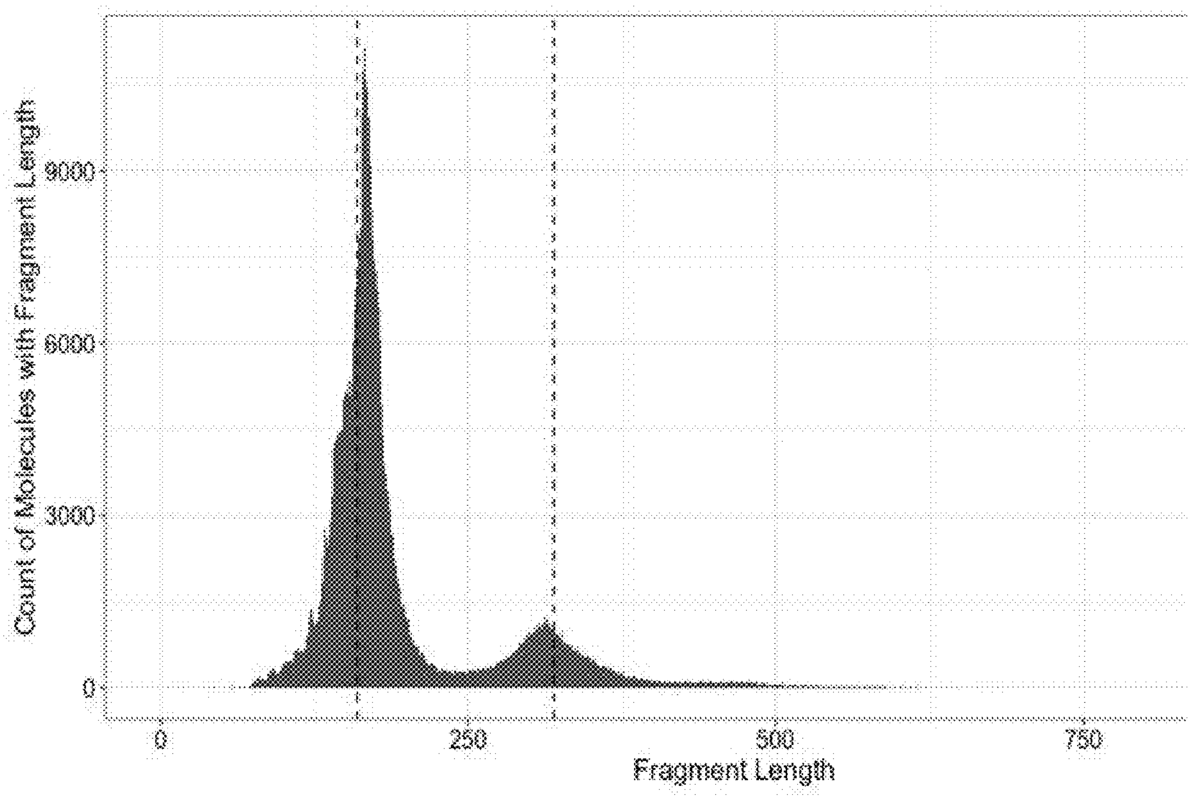
FIG. 11 shows fragment length distribution from cfDNA sample.

Synthetic cfDNA sample shows high repeatability in multiple assays at different targeted VAF levels. The manufacturing modifications from V1 to V2 showed an improvement in both the representation of DNA fragments across simulated variants as well as less variability in the fragment lengths (FIG. 9). The updates removed the periodic peak seen every 7 base pairs in v1 (FIG. 10) creating a more even distribution and decreased small (<150 bp) and large fragments (>200).

Dilution of the synthetic cfDNA variants with WT DNA show linearity and diluted with consistency. When 100% cfDNA stock was blended with WT normal plasma targeting a 5% sample the variant signal was undetectable. A dilution series was successfully created using a previously made 10% contrived sample of the synthetic cfDNA and cell line WT as the starting parental level and then using normal plasma WT to target the lower dilution levels of 0.1%-1.5%.

Utilization of the synthetic cfDNA sample has proved to be an extremely valuable and effective sample type in feasibility and verification studies.

Although the invention has been described with reference to the above examples, it will be understood that modifications and variations are encompassed within the spirit and scope of the invention. Accordingly, the invention is limited only by the following claims.

What is claimed is:

1. A method for validating assay performance of a next-generation sequencing (NGS) assay of interest comprising:

synthesizing synthetic variant DNA fragments comprising variants with known allele frequencies, wherein the variants occur throughout a genome, wherein the synthetic variant DNA fragments comprise a molecular barcode, wherein at least 20× synthetic variant DNA fragments are generated for each variant, and wherein the at least 20× synthetic variant DNA fragments span each variant based on a sliding window of increments with distinct start positions and end positions upstream and downstream of a targeted variant position;

combining the synthetic variant DNA fragments with wild-type (WT) DNA fragments to create a synthetic standard with an expected abundance of each variant with known allele frequency;

preparing one or more dilutions of the synthetic standard;

performing the NGS assay of interest on the one or more dilutions of the synthetic standard to measure an observed abundance of each variant with known allele frequency; and comparing the observed abundance of each variant with known allele frequency to the expected abundance of each variant with known allele frequency, thereby validating the performance of the NGS assay of interest.

2. The method of claim 1, wherein the variants are in exons.

3. The method of claim 1, wherein the WT DNA fragments are isolated from a biological sample selected from the group consisting of a cell line, a histological slide, a biopsy sample, a formalin-fixed paraffin-embedded (FFPE) tissue, a body fluid, feces, urine, plasma, serum, whole blood, isolated blood cells, and cells isolated from blood.

4. The method of claim 1, wherein the WT DNA fragments are selected from the group consisting of cell-free (cfDNA), circulating tumor DNA (ctDNA), mRNA, genomic DNA, and cDNA.

5. The method of claim 1, wherein the variants are germline or somatic variants.

6. The method of claim 1, wherein the NGS assay of interest is a cfDNA-based NGS assay.

7. The method of claim 1, wherein the synthetic variant DNA fragments comprise the molecular barcode at the 3' and 5' ends of each DNA fragment to distinguish from clinical DNA fragments.

8. The method of claim 1, wherein the variants are selected from the group consisting of single nucleotide variants (SNVs), INDELS, copy number variants (CNV), loss of heterozygosity (LOH), microsatellite instability (MSI), and translocations.

9. The method of claim 1, wherein each synthetic variant DNA fragment has approximately 8 bp spacing to represent a single variant.

10. The method of claim 1, wherein the synthetic variant DNA fragments are approximately 167 bp.

11. The method of claim 1, wherein the synthetic variant DNA fragments comprise a panel from approximately 10 to 500 genes.

12. The method of claim 11, wherein each gene comprises at least one mutation.

13. The method of claim 11, wherein one or more genes are selected from the group consisting of FGFR1, FGFR2, FGFR3, NTRK1, NTRK2, NTRK3, RET, ROS1, BRAF, BRCA1, BRCA2, epidermal growth factor receptor (EGFR), ERBB2, H3F3A, IDH1, IDH2, KIT, KRAS, MET, NRAS, PDGFR, and ALK.

14. The method of claim 1, wherein the synthetic variant DNA fragments comprise fragments having a modified base.

15. The method of claim 14, wherein the modified base is selected from the group consisting of 5-methylcytosine (5 mC), N4-methylcytosine (N4 mC), and/or 6-methyladenine (6 mA).

16. The method of claim 14, wherein the synthetic variant DNA fragments are composed of a varying fractional composition of individual fragments having one or more modified bases.

17. A method of detecting a disease or disorder, or severity of the disease or disorder, in a subject comprising:

validating the performance of a next-generation sequencing (NGS) assay of interest using a method comprising, synthesizing synthetic variant DNA fragments comprising variants with known allele frequencies, wherein the variants occur throughout a genome, wherein the synthetic variant DNA fragments comprise a molecular barcode, wherein at least 20× synthetic variant cfDNA fragments are generated for each variant, and wherein the at least 20× synthetic variant cfDNA fragments span each variant based on a sliding window of increments with distinct start positions and end positions upstream and downstream of a targeted variant position;

combining the synthetic variant DNA fragments with wild-type (WT) DNA fragments to create a synthetic standard with an expected abundance of each variant with known allele frequency;

preparing one or more dilutions of the synthetic standard;

performing the NGS assay of interest on the one or more dilutions of the synthetic standard to measure an observed abundance of each variant with known allele frequency; and comparing the observed abundance of each variant with known allele frequency to the expected abundance of each variant with known allele frequency, thereby validating the performance of the NGS assay of interest, wherein the NGS assay of interest detects the disease or disorder, or severity of the disease or disorder;

obtaining a sample from the subject; and performing the validated NGS assay on DNA of the sample from the subject and detecting a target of interest indicative of the disease or disorder, or severity of the disease or disorder, thereby detecting the disease or disorder, or severity of the disease or disorder in the subject.

18. The method of claim 17, wherein the target of interest is a genomic variant.

19. The method of claim 18, wherein the genomic variant is a mutant allele.

20. The method of claim 17, wherein the disease or disorder is cancer.

21. A method of detecting drug resistance in a subject comprising:

validating the performance of a next-generation sequencing (NGS) assay of interest using a method comprising, synthesizing synthetic variant DNA fragments comprising variants with known allele frequencies, wherein the variants occur throughout a genome, wherein the synthetic variant DNA fragments comprise a molecular barcode, wherein at least 20× synthetic variant cfDNA fragments are generated for each variant, and wherein the at least 20× synthetic variant cfDNA fragments span each variant based on a sliding window of increments with distinct start positions and end positions upstream and downstream of a targeted variant position;

combining the synthetic variant DNA fragments with wild-type (WT) DNA fragments to create a synthetic standard with an expected abundance of each variant with known allele frequency;

preparing one or more dilutions of the synthetic standard;

performing the NGS assay of interest on the one or more dilutions of the synthetic standard to measure an observed abundance of each variant with known allele frequency; and comparing the observed abundance of each variant with known allele frequency to the expected abundance of each variant with known allele frequency, thereby validating the performance of the NGS assay of interest, wherein the NGS assay of interest detects the drug resistance;

obtaining a sample from the subject; and performing the validated NGS assay on DNA of the sample from the subject and detecting a target of interest indicative of the drug resistance, thereby detecting the drug resistance in the subject.

22. The method of claim 21, wherein the drug is a chemotherapy drug.

23. The method of claim 1, wherein each synthetic variant DNA fragment contains at least two types of variants selecting from the group of an SNV, an INDEL, a translocation, and an amplification.

* * * * *